United States Patent [19]

Arold et al.

[11] 4,229,580
[45] Oct. 21, 1980

[54] PREPARATION OF 1-AZOLYL-3,3-DIMETHYL-1-PHENOXY-BUTAN-2-ONES

[75] Inventors: Hermann Arold; Hans-Ludwig Elbe; Eckart Kranz; Wolfgang Krämer; Jörg Stetter; Claus Stölzer; Rudolf Thomas, all of Wuppertal, Fed. Rep. of Germany

[73] Assignee: Bayer Aktiengesellschaft, Leverkusen, Fed. Rep. of Germany

[21] Appl. No.: 885,053

[22] Filed: Mar. 9, 1978

[30] Foreign Application Priority Data

Mar. 29, 1977 [DE] Fed. Rep. of Germany ....... 2713777

[51] Int. Cl.² .................. C07D 233/60; C07D 249/08
[52] U.S. Cl. ...................................... 548/262; 548/341
[58] Field of Search .................... 260/308 R; 548/341, 548/262

[56] References Cited

U.S. PATENT DOCUMENTS

| 3,912,752 | 10/1975 | Meiser et al. ..................... 260/308 R |
| 4,053,616 | 10/1977 | Buchel et al. ......................... 424/269 |

FOREIGN PATENT DOCUMENTS 2401715  7/1975  Fed. Rep. of Germany ...... 260/308 R

*Primary Examiner*—Alton D. Rollins

*Attorney, Agent, or Firm*—Sprung, Felfe, Horn, Lynch & Kramer

[57] ABSTRACT

In the reaction of 1-chloro-3,3-dimethylbutan-2-one with a phenol to form an ether-ketone, halogenating it to form a halogenoether-ketone and reacting it with imidazole or 1,2,4-triazole to form a 1-azolyl-3,3-dimethyl-1-phenoxybutan-2-one of the formula

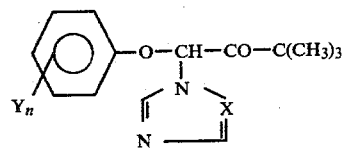

in which
  X is N or CH,
  n is an integer from 0 to 4, and
  Y each independently is halogen, phenyl, phenoxy, nitro, alkyl, alkoxy or cycloalkyl, the improvement which comprises effecting all steps successively in an aromatic hydrocarbon or chlorinated aliphatic or aromatic hydrocarbon as solvent without intermediate isolation. The products are obtained in high yield.

16 Claims, No Drawings

PREPARATION OF 1-AZOLYL-3,3-DIMETHYL-1-PHENOXY-BUTAN-2-ONES

The present invention relates to an unobvious process for the preparation of certain known fungicidal 1-azolyl-3,3-dimethyl-1-phenoxy-butan-2-ones.

It has already been disclosed that 1-azolyl-3,3-dimethyl-1-phenoxy-butan-2-ones are obtained when chloropinacolone is heated under reflux in a 1st stage for several hours with phenols in the presence of an acid acceptor in ketones, for example acetone, as solvents, the resulting 3,3-dimethyl-1-phenoxy-butan-2-ones are halogenated in the customary manner in a 2nd stage in the presence of a solvent which is inert towards halogenating agents, such as, in particular, chlorinated hydrocarbons, for example carbon tetrachloride, and finally the 1-chloro(bromo)-3,3-dimethyl-1-phenoxy-butan-2-ones thereby formed are reacted in a 3rd stage with azoles in the presence of polar solvents, such as, in particular, ketones, for example acetone, and in the presence of an acid acceptor at temperatures between 20° and 120° C. (see German Offenlegungsschriften (German Published Specifications) Nos. 2,105,490 and 2,401,715, and U.S. Pat. No. 3,912,752).

However, this aforesaid process has a number of disadvantages. Thus, the 3,3-dimethyl-1-phenoxy-butan-2-ones obtained in the first stage and the 1-halogeno-3,3-dimethyl-1-phenoxy-butan-2-ones obtained in the second stage must be isolated in each case, since the following reaction proceeds in an optimum manner only in another solvent, whereby a multi-stage process results.

The end product can be isolated and purified only after changing the solvent again, and by means of various successive washing operations which cause heavy pollution of the effluent.

Using various solvents gives rise to an increased expenditure of time, with respect to the working up, and thus higher production costs. These are also considerably increased by very long reaction times. Thus, this process in its entirety is very uneconomical. Added to this are the frequently unsatisfactory yields.

Furthermore, it has been disclosed that 3,3-dimethyl-1-phenoxy-1-(1,2,4-triazol-1-yl)-butan-2-ones are also obtained when a dihalogenopinacolone is reacted with 1,2,4-triazole and with phenols in the presence of an acid-binding agent and a diluent at temperatures between 0° and 150° C. (see German Offenlegungsschrift (German Published Specification) No. 2,406,665).

This prior art process has the disadvantage that competing reactions lead to a greater formation of by-products which considerably lower the yield (at most about 75%) and make a troublesome and time-consuming working up necessary.

The present invention now provides a process for the preparation of a 1-azolyl-3,3-dimethyl-1-phenoxy-butan-2-one of the general formula

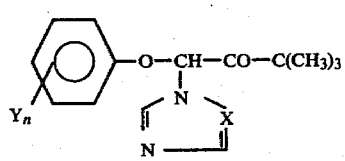    (I), in which
X represents a nitrogen atom or the CH group,
n represents 0, 1, 2, 3 or 4 and
Y represents halogen, phenyl, phenoxy, nitro, alkyl, alkoxy or cycloalkyl, the Y's being selected independently of one another when n is 2 or more,
in which 1-chloro-3,3-dimethylbutan-2-one (chloropinacolone), of the formula

    (II), is reacted with a phenol of the formula

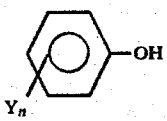    (III), in which
Y and n have the meanings stated above,
in the presence of an aromatic hydrocarbon or chlorinated aliphatic or aromatic hydrocarbon as a solvent, and in the presence of an acid acceptor, at a temperature of about 60° to 150° C., the ether-ketone formed of the general formula

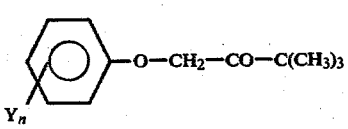    (IV), in which
Y and n have the meanings stated above,
is reacted, without isolation, with a halogenating agent in the presence of the same solvent at a temperature of about 20° to 60° C., and finally the halogenether-ketone thereby formed of the general formula

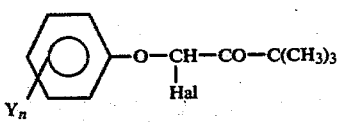    (V), in which
Y and n have the meanings stated above and
Hal represents halogen, especially chlorine or bromine,
is reacted, also without isolation, with an azole of the general formula

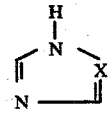    (VI), in which
X has the meaning stated above,
in the presence of the same solvent and in the presence of an acid acceptor at a temperature of about 20° to 120° C.

It is quite surprising that the 1-azolyl-3,3-dimethyl-1-phenoxy-butan-2-ones of the formula (I) can be formed in high yield and purity under the conditions of the process according to the invention, since in the light of the state of the art it had to be expected that it would be possible to arrive at these compounds only when the solvent is changed four times, especially since it is generally known that nucleophilic substitutions of α-halogenoketones proceed particularly well in polar organic solvents, such as ketones, for example acetone, or amides, for example dimethylformamide, or nitriles, for example acetonitrile. The successful use of, in particular, an aromatic or chlorinated aliphatic or aromatic hydrocarbon as the solvent for all the individual reactions is all the more surprising.

The process according to the invention has a number of advantages. Thus, it is a true "one pot process", in which neither are the intermediate products isolated, nor is the solvent changed.

Reaction times and working-up times which are shortened by more than half, recovery of only one solvent, small amounts of effluent and, additionally, a low salt load, and high yields of 94% and over, associated with high purity all make the process according to the invention a very economical one.

If chloropinacolone and 4-chlorophenol are used as starting materials, sulphuryl chloride is used as the halogenating agent, 1,2,4-triazole is used as the azole and toluene is used as the solvent, the course of the reaction can be represented by the following equation:

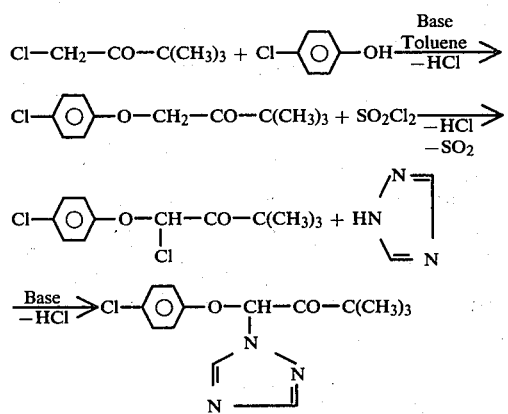

The formula (III) provides a general definition of the phenols used as starting compounds. Preferably in this formula, Y represents chlorine, bromine, fluorine, phenyl, phenoxy, nitro, straight-chain or branched alkyl or alkoxy with up to 4 carbon atoms in each case, or cycloalkyl with 5 or 6 carbon atoms, and the n represents 0, 1, 2 or 3.

Solvents which can be used for the process according to the invention are aromatic hydrocarbons, such as benzene, toluene, xylene or nitrobenzene; chlorinated aromatic hydrocarbons, such as chlorobenzene, dichlorobenzene or chlorotoluene; and chlorinated aliphatic hydrocarbons, such as dichloroethane. The aromatic hydrocarbons, such as, for example, toluene, are particularly preferred.

A halogenating agent which can be used for the process according to the invention is sulphuryl chloride.

The azoles of the formula (VI) are 1,2,4-triazole and imidazole.

The process according to the invention is preferably carried out in the presence of an inorganic acid-binding agent, such as, for example, an alkali metal carbonate. Dry, powdered potassium carbonate is preferably used here. In the case of the reaction with 1,2,4-triazole or imidazole, an appropriate excess of the particular azole can also be employed.

The reaction temperatures can be varied within a relatively wide range. In general, the first process step (reaction with a phenol) is carried out at from 60° to 150° C., preferably at about 80° to 120° C., the second process step (halogenation) is carried out at from 20° to 60° C., preferably at about 30° to 50° C., and the third process step (reaction with an azole) is carried out at from 20° to 120° C., preferably at about 60° to 110° C.

In carrying out the process according to the invention, about 1 to 1.2 moles of a phenol of the formula (III) and about 1 to 2 moles of an acid-binding agent are preferably employed per mole of 1-chloro-3,3-dimethylbutan-2-one, and about 1 mole of a halogenating agent, about 1 to 1.2 moles of 1,2,4-triazole or imidazole and about 1 to 1.2 moles of an acid-binding agent are preferably added in the course of the reaction. Higher or lower amounts of up to about 20 mol percent can be used without substantially lowering the yield.

In order to isolate the active compounds prepared according to the invention, water is added to the reaction mixture and the mixture is stirred until the water-soluble proportion of solid material is dissolved. After separating off the aqueous layer, the organic phase is treated with dilute alkali metal hydroxide solution and finally washed until neutral. The solvent can be removed by counter-current steam distillation and the residue can be purified by recrystallization.

The active compounds according to the invention are distinguished, as is known, by a very good fungicidal activity (compare U.S. Pat. Nos. 3,912,752 and 3,898,341).

Thus, for example, they can be used with particularly good success as agents against powdery mildew (as a leaf fungicide) and against cereal diseases, such as cereal rust (as a seed dressing).

The active compounds can be converted into the customary formulations, such as solutions, emulsions, suspensions, powders, pastes and granules.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The formulations in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

The process according to the invention is illustrated in the following examples:

EXAMPLE 1

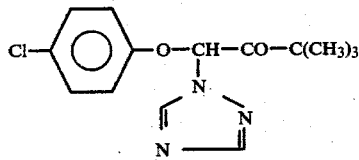

(1)

A. (solvent: toluene)

3 kg of toluene, 1.2 kg (9.4 mol) of 4-chlorophenol and 1.25 kg (9 mol) of potassium carbonate were initially introduced into a 12 liter flask with a water separator, stirrer, thermometer and dropping funnel, and the contents of the flask were warmed to 90° C. by means of a heating bath, while stirring. 1.2 kg (9 mol) of 1-chloro-3,3-dimethylbutan-2-one were added at 90° C. in the course of one hour. The contents of the flask were then heated to the boiling point (about 115° to 120° C.) for 6 hours and about 100 ml of water were distilled off azeotropically via a water separator.

Thereafter, the mixture was cooled to 40° C. and 6 kg of water were added to the contents of the flask. The mixture was stirred at 20° to 30° C. until the solid material had dissolved, and the aqueous phase was then separated off. The organic phase remaining in the flask was dried by distillation via a water separator. Thereafter, 1.2 kg (9 mol) of sulphuryl chloride were added to the residue at 30° to 35° C. in the course of 6 hours, and the mixture was stirred for a further 3 hours at 35° C. In order to remove the excess sulphuryl chloride, the partially dissolved gaseous hydrochloric acid and the sulphur dioxide, 400 ml of toluene were distilled off under about 50 mm Hg.

1.3 kg (18.8 mol) of 1,2,4-triazole were then added to the contents of the flask and the mixture was stirred for 6 hours at 95° C. After cooling to 20°–30° C., the contents of the flask were stirred with 2.5 kg of water until the water-soluble solid material had dissolved. The aqueous phase was separated off, the organic phase was washed twice with 1.5 kg of 5% strength sodium hydroxide solution each time and once with 1.5 kg of water at 20° to 30° C., and the solvent was then stripped off. This gave, as the residue, 2.4 kg (94.1% of theory) of 1-(4-chlorophenoxy)-3,3-dimethyl-1-(1,2,4-triazol-1-yl)-butan-2-one of melting point 75°–76° C. in 97% purity (determined by gas chromatography).

B. (solvent: dichloroethane)

3 kg of dichloroethane, 0.67 kg (5.2 mol) of 4-chlorophenol and 1.35 kg (9.8 mol) of potassium carbonate were initially introduced into a 12 liter flask with a water separator, stirrer, thermometer and dropping funnel, and the contents of the flask were warmed to 80° C. by means of a heating bath, while stirring. 0.67 kg (5 mol) of 1-chloro-3,3-dimethylbutan-2-one was added at 80° C. in the course of 1 hour. The contents of the flask were then heated to the boiling point (about 85° C. to 88° C.) for 6 hours, and about 50 ml of water were distilled off azeotropically via the water separator.

Thereafter, the mixture was cooled to 40° C., and 7 kg of water were added to the contents of the flask. The mixture was stirred at 20° to 30° C. until the solid material had dissolved, and the aqueous phase was then separated off. The organic phase remaining in the flask was dried by distillation via the water separator. Thereafter, 0.67 kg (5 mol) of sulphuryl chloride was added at 30° to 35° C. in the course of 6 hours and the mixture was stirred for a further 3 hours at 35° C.

In order to remove the excess sulphuryl chloride, the partially dissolved gaseous hydrochloric acid and the sulphur dioxide, 400 ml of 1,2-dichloroethane were distilled off under normal pressure. 0.76 kg (11 mol) of 1,2,4-triazole was then added to the contents of the flask and the mixture was stirred for 6 hours at 85° C. After cooling to 20° to 30° C., the contents of the flask were stirred with 1.5 kg of water until the water-soluble solid material had dissolved. The aqueous phase was separated off, the organic phase was washed twice with 0.9 kg of 5% strength sodium hydroxide solution each time and once with 0.9 kg of water at 20° to 30° C., and the solvent was then stripped off. This gave, as the residue, 1.39 kg (94.9% of theory) of 1-(4-chlorophenoxy)-3,3-dimethyl-1-(1,2,4-triazol-1-yl)-butan-2-one of melting point 75°–76° C. in 95.5% purity (determined by gas chromatography).

EXAMPLE 2

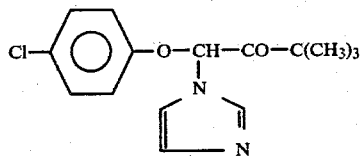

(2)

3 kg of toluene, 1.2 kg (9.4 mol) of 4-chlorophenol and 1.25 kg (9 mols) of potassium carbonate were initially introduced into a 12 liter flask with a water separator, stirrer, thermometer and dropping funnel, and the contents of the flask were warmed to 90° C. by means of a heating bath, whilst stirring. 1.2 kg (9 mol) of 1-chloro-3,3-dimethylbutan-2-one were added at 90° C. in the course of 1 hour. The contents of the flask were then heated to the boiling point (about 115° to 120° C.) for 6 hours, and about 100 ml of water were distilled off azeotropically via the water separator. Thereafter, the mixture was cooled to 40° C. and 6 kg of water were added to the contents of the flask. The mixture was stirred at 20° to 30° C. until the solid material had dissolved, and the aqueous phase was then separated off. The organic phase remaining in the flask was dried by distillation via the water separator.

Thereafter, 1.2 kg (9 mol) of sulphuryl chloride were added at 30° to 35° C. in the course of 6 hours and the mixture was stirred for a further 3 hours at 35° C. In order to remove the excess sulphuryl chloride, the partially dissolved gaseous hydrochloric acid and the sulphur dioxide, 400 ml of toluene were distilled off under about 50 mm Hg. 1.3 kg (19.1 mol) of imidazole were then added to the contents of the flask and the mixture was stirred for 6 hours at 95° C. After cooling to 20° to 30° C., 2.5 kg of water were added to the contents of the flask, and the mixture was stirred until the solid material had dissolved to the extent that the turbidity was slight. The aqueous phase was separated off, the organic phase was washed twice with 1.5 kg of 5% strength sodium hydroxide solution each time and once with 1.5 kg of water at 20°–30° C., and the solvent was then stripped off. This gave, as the residue, 2.47 kg (94% of theory) of 1-(4-chlorophenoxy)-3,3-dimethyl-1-imidazol-1-yl-butan-2-one of melting point 97° C. in 96.5% purity (determined by gas chromatography).

EXAMPLE 3

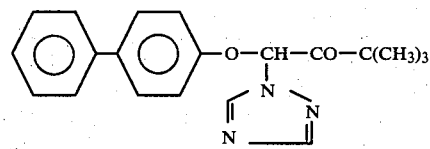
(3)

3.5 kg of toluene, 1.702 kg (10 mol) of 4-phenylphenol and 0.755 kg (5.4 mol) of potassium carbonate were initially introduced into a 10 liter flask with a water separator, stirrer, thermometer and dropping funnel.

1,366 kg (10 mol) of 1-chloro-3,3-dimethylbutan-2-one were added at about 20° C. The contents of the flask were then heated to the boiling point (about 115° to 120° C.) for 16 hours, while stirring, and about 160 ml of water were distilled off azeotropically via the water separator.

Thereafter, the mixture was cooled to 40° C. and 3.5 kg of water were added to the contents of the flask. The mixture was stirred at 20° to 30° C. until the solid material had dissolved, and 0.15 kg of 30% strength hydrochloric acid was added, the mixture was stirred for 15 minutes and the aqueous phase was then separated off. The organic phase remaining in the flask was dried by distillation via the water seprator.

After adding 1.5 kg of toluene, 1.35 kg (10 mol) of sulphuryl chloride were added at 40° to 45° C. in the course of 6 hours, and the mixture was stirred for a further 14 hours at 45° to 50° C. In order to remove the excess sulphuryl chloride, the partially dissolved gaseous hydrochloric acid and the sulphur dioxide, 600 ml of toluene were distilled off under about 50 mm Hg.

3.5 kg of toluene and 1.38 kg (20 mol) of 1,2,4-triazole were then added to the contents of the flask, and the mixture was stirred for 10 hours at 90° C. After cooling to 20° to 30° C., the contents of the flask were stirred with 2.5 kg of water until the water-soluble solid material had dissolved. After filtration, the aqueous phase was separated off, the organic phase was washed twice with 1.5 kg of 5% strength sodium hydroxide solution each time and once with 1.5 kg of water at 20° to 30° C., and the solvent was then stripped off. This gave, as the residue, 3.29 kg (98.2% of theory) of 1-(4-biphenylyloxy)-3,3-dimethyl-1-(1,2,4-triazol-1-yl)-butan-2-one of melting point 105°–106° C. in 96% purity (determined by gas chromatography).

The compounds of Table 1 were obtained in an analogous manner.

TABLE 1

![Structure I]

| Compound No. | $Y_n$ | X | Melting point (°C.) or boiling point (°C./mm Hg column) |
|---|---|---|---|
| 4 | 4-F | N | 160/0.3 |
| 5 | 4-Br | N | 89-92 |
| 6 | 4-NO₂ | N | 145 |
| 7 | 2,4-Cl₂ | N | 65 |
| 8 | 3-Cl | N | 65-67 |
| 9 | 4-Br, 2-Cl | N | 94-96 |
| 10 | 2-OCH₃ | N | 87 |
| 11 | 2,4-(CH₃)₂ | N | 74 |
| 12 | 3,4-Cl₂ | N | 82-84 |
| 13 | 3-Cl, 4-NO₂ | N | 100-104 |
| 14 | 2-CH₃, 5-NO₂ | N | 154 |
| 15 | | N | 125 |
| 16 | 2-Br, 4—⟨O⟩ | N | 98-99 |
| 17 | 4- ⟨H⟩ | N | 107 |
| 18 | 2- ⟨H⟩ | N | 98 |
| 19 | 4-O—⟨O⟩ | N | 149-150 |
| 20 | 2,6-Cl₂, 4—⟨O⟩ | N | 150-160 (.HCl) |
| 21 | 2,4,6-Cl₃ | N | 107 |
| 22 | 2-Cl, 4—⟨O⟩ | CH | 147/0.01 |
| 23 | — | CH | 172 |
| 24 | 3-Cl | CH | 106 |
| 25 | 4-Br | CH | 166/0.01 |
| 26 | 4-F | CH | 151 |
| 27 | 4-NO₂ | CH | 140 (.HCl) |
| 28 | 4-C(CH₃)₃ | CH | 105 |
| 29 | 2—⟨O⟩ | CH | 104 |
| 30 | 4—⟨O⟩ | CH | 69 |
| 31 | 2,4-Cl₂ | CH | 119 |
| 32 | 2,6-Cl₂ | CH | 146 |
| 33 | 2,5-Cl₂ | CH | 155 |
| 34 | 2-Cl, 6—⟨O⟩ | CH | 123 (.HCl) |
| 35 | 4-Br, 2-Cl | CH | 231 (.HCl) |
| 36 | 2-CH₃, 5-NO₂ | CH | 200-201 |
| 37 | 2-Cl, 4—⟨O⟩ | CH | 112-115 |
| | 2,6-Cl₂, 4—⟨O⟩ | | |

TABLE 1-continued

| Compound No. | $Y_n$ | X | Melting point (°C.) or boiling point (°C./mm Hg column) |
|---|---|---|---|
| 38 | 4-I | CH | 90–91 |
| 39 | 4-O—⌬ | CH | 94–97 |

It will be appreciated that the instant specification and examples are set forth by way of illustration and not limitation, and that various modifications and changes may be made without departing from the spirit and scope of the present invention.

What we claim is:

1. A process for the preparation of a 1-azolyl-3,3-dimethyl-1-phenoxy-butan-2-one of the formula

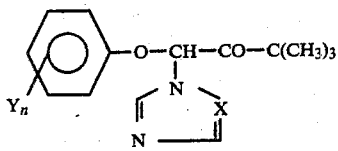

in which
X is N or CH,
n is an integer from 0 to 4, and
Y each independently is halogen, phenyl, phenoxy, nitro, alkyl, alkoxy or cycloalkyl,
comprising in a first step reacting 1-chloro-3,3-dimethylbutan-2-one of the formula Cl—CH$_2$—CO—C(CH$_3$)$_3$ with a phenol of the formula

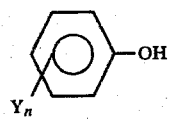

in the presence of an aromatic hydrocarbon or chlorinated aliphatic or aromatic hydrocarbon as solvent, and in the presence of an acid acceptor, at a temperature of about 60° to 150° C. thereby to form an ether-ketone of the formula

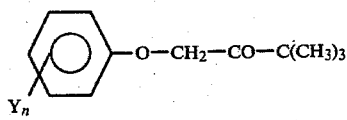

without isolation in a second step reacting the ether-ketone with a chlorinating agent in the presence of the same solvent at a temperature of about 20° to 60° C. thereby to form a chloroether-ketone of the formula

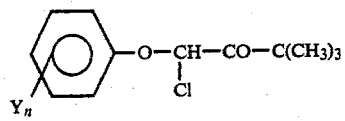

and without isolation in a third step reacting the chloroether-ketone with an azole of the formula

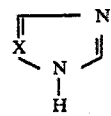

in the presence of the same solvent and in the presence of an acid acceptor at a temperature of about 20° to 120° C.

2. A process according to claim 1, in which toluene is used as the solvent.

3. A process according to claim 1, in which dichloroethane is used as the solvent.

4. A process according to claim 1, in which benzene, xylene, nitrobenzene, chlorobenzene, dichlorobenzene or chlorotoluene is used as the solvent.

5. A process according to claim 1, in which
Y is chlorine, bromine, fluorine, phenyl, phenoxy, nitro, alkyl or alkoxy with up to 4 carbon atoms, or cycloalkyl with 5 or 6 carbon atoms, and
n is an integer from 0 to 3.

6. A process according to claim 1 in which the first step is effected in the presence of an alkali metal carbonate as acid-binding agent.

7. A process according to claim 6, in which the acid-binding agent is potassium carbonate.

8. A process according to claim 1 in which the chlorinating agent is sulphuryl chloride.

9. A process according to claim 1 in which the third step is effected in the presence of an alkali metal carbonate or an excess of the azole as acid-binding agent.

10. A process according to claim 5 in which the solvent is toluene, dichloroethane, benzene, xylene, nitrobenzene, chlorobenzene, dichlorobenzene or chlorotoluene, there are employed, per mole of 1-chloro-3,3-dimethyl-butan-2-one, about 1 to 1.2 moles of the phenol and about 1 to 2 moles of potassium carbonate as acid-binding agent in the first step which is effected at a temperature of about 80° to 120° C., about 1 mole of sulphuryl chloride as chlorinating agent in the second step which is effected at a temperature of about 30° to 50° C., and about 1 to 1.2 moles of the azole and about 1 to 1.2 moles of alkali metal carbonate or further azole as acid-binding agent in the third step which is effected at a temperature of about 60° to 110° C.

11. A process according to claim 1, wherein
X is N, and
Y is 4-chloro.

12. A process according to claim 1, wherein
X is CH, and
Y is 4-chloro.

13. A process according to claim 1, wherein
X is N, and
Y is 4-phenyl.

14. A process according to claim 1, wherein
X is N, and
Y is 2,4-dichloro.

15. A process according to claim 1, wherein
X is CH, and
Y is 4-phenyl.

16. A process according to claim 1, wherein
X is CH, and
Y is 2,4-dichloro.

* * * * *